(12) United States Patent
Ziff et al.

(10) Patent No.: US 11,633,097 B1
(45) Date of Patent: Apr. 25, 2023

(54) AUTOMATED METHOD FOR TESTING PERIPHERAL AND EXPANDED VISUAL FIELDS ON LIMITED FIELD OF VIEW HEAD-MOUNTED DEVICE

(71) Applicant: Mongoose Enterprises, LLC, Miami, FL (US)

(72) Inventors: Matteo Ziff, Miami, FL (US); Alana Grajewski, Miami, FL (US)

(73) Assignee: Mongoose Enterprises, LLC, Miami, FL (US)

( * ) Notice: Subject to any disclaimer, the term of this patent is extended or adjusted under 35 U.S.C. 154(b) by 0 days.

(21) Appl. No.: 17/698,464

(22) Filed: Mar. 18, 2022

(51) Int. Cl.
*A61B 3/024* (2006.01)
*A61B 3/00* (2006.01)

(52) U.S. Cl.
CPC .............. *A61B 3/024* (2013.01); *A61B 3/005* (2013.01); *A61B 3/0008* (2013.01); *A61B 3/0091* (2013.01)

(58) Field of Classification Search
CPC ....... A61B 3/024; A61B 3/0008; A61B 3/005; A61B 3/0091

USPC ........................................................ 351/246
See application file for complete search history.

(56) References Cited

U.S. PATENT DOCUMENTS

| | | | |
|---|---|---|---|
| 10,292,580 B2 * | 5/2019 | Hetling | A61B 5/378 |
| 10,444,514 B2 | 10/2019 | Abou Shousha et al. | |
| 10,531,795 B1 | 1/2020 | Abou Shousha | |
| 11,102,462 B2 | 8/2021 | Abou Shousha | |
| 2013/0141697 A1 * | 6/2013 | Berry | G16H 10/60 |
| | | | 351/242 |
| 2017/0049316 A1 * | 2/2017 | Donaldson | A61B 3/0033 |

\* cited by examiner

*Primary Examiner* — Mohammed A Hasan
(74) *Attorney, Agent, or Firm* — Albert Bordas P.A.

(57) ABSTRACT

An automated method for testing peripheral and expanded visual fields on limited field of view head-mounted device. The method has a fixation point that is placed in multiple locations of the field of view to test stimuli points that would be outside of the field of view of a head-mounted device if the fixation point were in the center. Stimuli points are grouped together and are associated with fixation points. Each stimulus appears individually on an opposite side of the fixation point in the field of view. The stimuli points may be static or dynamic. The method is applied as visual field diagnostic tool for Ptosis disorder, Esterman test, or any expanded peripheral Visual Field test.

20 Claims, 13 Drawing Sheets

AUTOMATED METHOD FOR TESTING PERIPHERAL AND EXPANDED VISUAL FIELDS ON LIMITED FIELD OF VIEW HEAD-MOUNTED DEVICE

BACKGROUND OF THE INVENTION

Field of the Invention

The present invention relates to visual field testing methods and systems, and more particularly, to automated methods and systems for testing peripheral and expanded visual fields.

Description of the Related Art

Applicant believes that one of the closest references corresponds to U.S. Pat. No. 10,444,514 B2 issued to Abou Shousha et al. on Oct. 15, 2019, for Field of view enhancement via dynamic display portions. However, it differs from the present invention because Abou teaches an enhancement of a field of view of a user that may be facilitated via one or more dynamic display portions. One or more changes related to one or more eyes of a user may be monitored. Based on the monitoring, one or more positions of one or more transparent display portions of a screen of wearable device may be adjusted, where the transparent display portions enable the user to see through the screen of the wearable device.

Applicant believes that one of the closest references corresponds to U.S. Pat. No. 10,531,795 B1 issued to Abou Shousha on Jan. 14, 2020, for Vision defect determination via a dynamic eye-characteristic-based fixation point. However, it differs from the present invention because Abou teaches a vision defect information that may be generated via a dynamic eye-characteristic-based fixation point. A first stimulus may be displayed at a first location on a user interface based on a fixation point for a visual test presentation. The fixation point for the visual test presentation may be adjusted during the visual test presentation based on eye characteristic information related to a user. The eye characteristic information may indicate a characteristic of an eye of the user that occurred during the visual test presentation. A second stimulus may be displayed during the visual test presentation at a second interface location on the user interface based on the adjusted fixation point for the visual test presentation. Vision defect information associated with the user may be generated based on feedback information indicating feedback related to the first stimulus and feedback related to the second stimulus.

Applicant believes that one of the closest references corresponds to U.S. Pat. No. 11,102,462 B2 issued to Abou Shousha on Aug. 24, 2021, for Vision defect determination via a dynamic eye characteristic-based fixation point. However, it differs from the present invention because Abou teaches a vision defect information that may be generated via a dynamic eye-characteristic-based fixation point. A first stimulus may be displayed at a first location on a user interface based on a fixation point for a visual test presentation. The fixation point for the visual test presentation may be adjusted during the visual test presentation based on eye characteristic information related to a user. The eye characteristic information may indicate a characteristic of an eye of the user that occurred during the visual test presentation. A second stimulus may be displayed during the visual test presentation at a second interface location on the user interface based on the adjusted fixation point for the visual test presentation. Vision defect information associated with the user may be generated based on feedback information indicating feedback related to the first stimulus and feedback related to the second stimulus.

Other patents describing the closest subject matter provide for a number of more or less complicated features that fail to solve the problem in an efficient and economical way. None of these patents suggest the novel features of the present invention.

SUMMARY OF THE INVENTION

The present invention is an automated method for testing peripheral and expanded visual fields on limited field of view head-mounted device, comprising the steps of:

A) displaying a virtual introduction on performing a peripheral visual field test on a head-mounted device, whereby the head-mounted device comprises a computer having virtual reality software to operate virtual reality visual field testing;

B) providing a virtual interactive tutorial automatically;

C) beginning the peripheral visual fields test automatically after the virtual interactive tutorial;

D) showing a fixation point at a first location in field of view automatically for a patient to focus on for a duration of the peripheral visual field test;

E) displaying a first sequence of stimuli points for the first location of the fixation point automatically;

F) clicking on a trigger of a controller by the patient when the stimuli points are seen;

G) showing the fixation point at a second location of the field of view automatically for the patient to focus on for the duration of the peripheral visual field test;

H) displaying a second sequence of the stimuli points for the second location of the fixation point automatically;

I) clicking on the trigger of the controller by the patient when the stimuli points are seen;

J) showing the fixation point at a third location of the field of view automatically for the patient to focus on for the duration of the peripheral visual field test;

K) displaying a third sequence of the stimuli points for the third location of the fixation point automatically;

L) clicking on the trigger of the controller by the patient when the stimuli points are seen;

M) placing the fixation point at additional different locations sequentially and automatically until all predetermined sequences of the stimuli points have been tested;

N) ending the peripheral visual field test.

The virtual introduction comprises instructions about the fixation point, the stimuli points, a head-mounted device adjustment, and a controller adjustment. The virtual introduction is through virtual graphics, virtual images, audio, and text. The fixation point can be displayed as an image or a colored light. The fixation point can be displayed as a glowing and dampening colored light. The fixation point can be animated. The patient views a monocular or binocular viewing of the fixation point. A single fixation point is displayed at a time. The fixation point is automatically removed or moved after testing a corresponding sequence of the stimuli points.

The stimuli points produce a light stimulus. The stimuli points are dynamic or static. The stimuli points automatically blink or move to predetermined locations. The stimuli points are part of a grid of points. The grid of points has a predetermined size. The stimuli points on the grid of points are automatically spaced a predetermined distance. The stimuli points are automatically grouped. The fixation point is associated with a grouping of the stimuli points. The stimuli points follow a semi-random schedule for appearance. The stimuli points appear on an opposite side of the fixation point on the field of view. The fixation point is placed in multiple locations of the field of view for testing the stimuli points that are outside of the field of view of a head-mounted device if the fixation point is in the center of the field of view.

It is therefore one of the main objects of the present invention to provide an automated method for testing peripheral and expanded visual fields on limited field of view head-mounted device.

It is another object of this invention to provide an automated method for testing peripheral and expanded visual fields on limited field of view head-mounted device in which fixation points are moved to different locations of a grid.

It is another object of this invention to provide an automated method for testing peripheral and expanded visual fields on limited field of view head-mounted device, which has a virtual introduction on how to perform a visual field test allowing the test to be administered without specialized technicians.

It is another object of this invention to provide an automated method for testing peripheral and expanded visual fields on limited field of view head-mounted device, which has an interactive tutorial of an expanded field of view test.

It is another object of this invention to provide an automated method for testing peripheral and expanded visual fields on limited field of view head-mounted device in which the entire process is automated and does not require any manual work, instructions, or interaction other than from the patient.

It is another object of this invention to provide an automated method for testing peripheral and expanded visual fields on limited field of view head-mounted device, which is used as a Visual Field Diagnostic tool for Ptosis disorder, Esterman Test, or any expanded peripheral Visual Field test.

It is another object of this invention to test peripheral and expanded visual fields on limited field of view head-mounted device in which fixation points are placed in multiple areas for testing corresponding stimuli points that would be outside of the field of view when the fixation point is in the center of the field of view.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

V. DETAILED DESCRIPTION OF THE INVENTION

Figure 1:
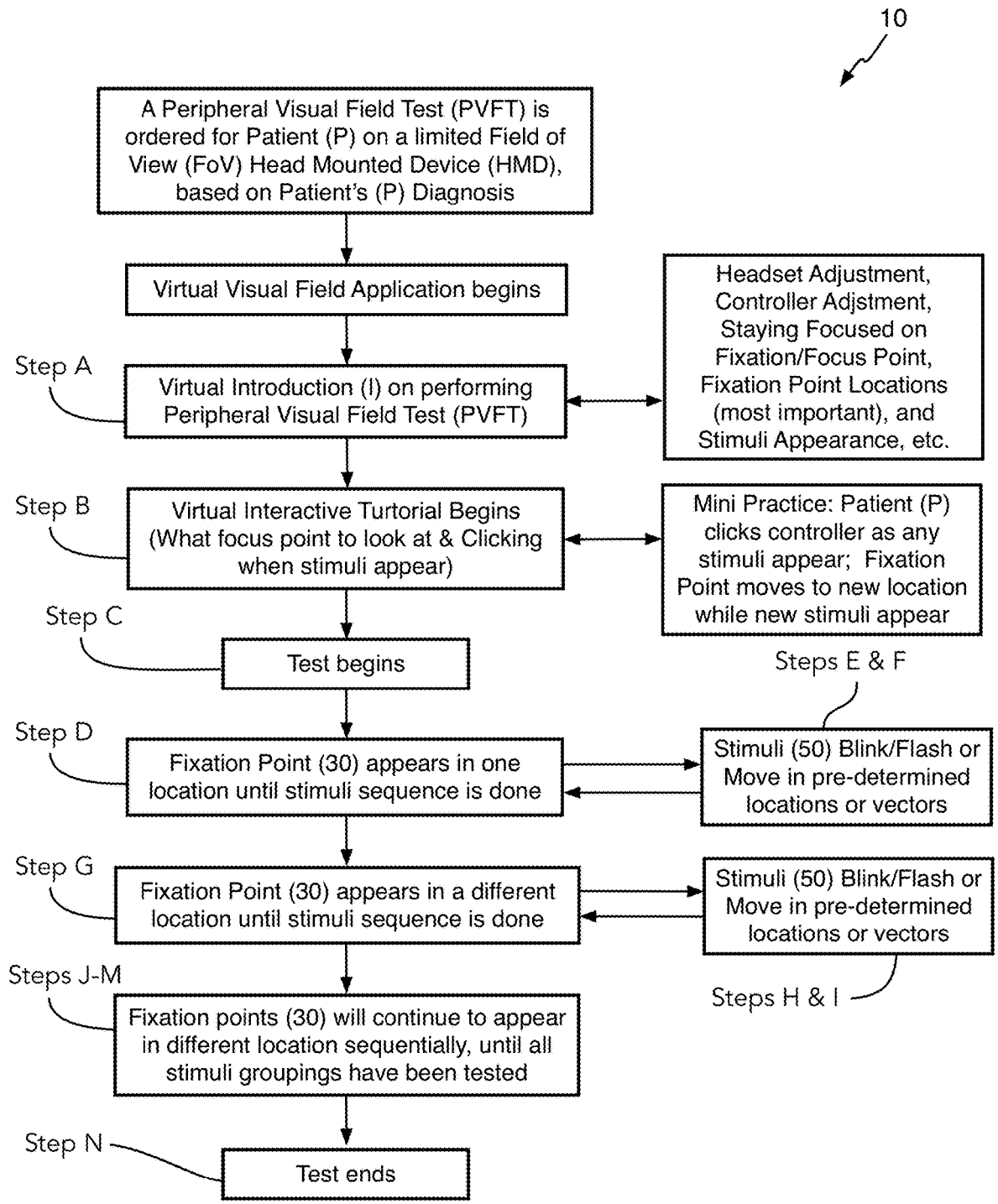
FIG. 1 is a flow chart representing a method of the present invention.

Referring now to the drawings, the present invention is an automated method for testing peripheral and expanded visual fields on limited field of view head-mounted devices, and is generally referred to with numeral 10.

As seen in FIG. 1, present invention 10, comprises the steps of:

A) displaying a virtual introduction I on performing a peripheral visual field test PVFT on a head-mounted device HMD, whereby said head-mounted device HMD comprises a computer having virtual reality software to operate virtual reality visual field testing;

B) providing a virtual interactive tutorial automatically;

C) beginning the peripheral visual field test PVFT automatically after said virtual interactive tutorial;

D) showing fixation point 30 at a first location of field of view 22 automatically for patient P to focus on for a duration of the peripheral visual field test PVFT;

E) displaying a first sequence of stimuli points 50 for a first location of fixation point 30 automatically;

F) clicking on a trigger of a controller by patient P when stimuli points 50 are seen;

G) showing fixation point 30 at a second location of field of view 22 automatically for patient P to focus on for the duration of the peripheral visual field test PVFT;

H) displaying a second sequence of stimuli points 50 for a second location of fixation point 30 automatically;

I) clicking on the trigger of the controller by patient P when stimuli points 50 are seen;

J) showing fixation point 30 at a third location of field of view 22 automatically for patient P to focus on for the duration of the peripheral visual field test PVFT;

K) displaying a third sequence of stimuli points 50 for a third location of fixation point 30 automatically;

L) clicking on the trigger of the controller by patient P when stimuli points 50 are seen;

M) placing fixation point 30 at additional different locations sequentially and automatically until all predetermined sequences of stimuli points 50 have been tested;

N) ending the peripheral visual field test PVFT.

Step A) displaying a virtual introduction I on performing a peripheral visual field test PVFT on a head-mounted device HMD, whereby said head-mounted device HMD comprises a computer having virtual reality software to operate virtual reality visual field testing, comprises instructions on how to perform the peripheral visual field test PVFT. This allows for the peripheral visual field test PVFT according to present invention 10 to be administered without specialized technicians. Virtual introduction I comprises instructions about fixation point 30, stimuli points 50, a head-mounted device HMD adjustment, a controller adjustment, and more.

As presented above, head-mounted device HMD comprises a computer. The computer of the present invention 10 comprises at least hardware for Virtual Reality: Processor (CPU), Video Card (GPU), Memory (RAM), Storage (Drives). The two main factors in virtual reality performance are the CPU (central processing unit, often referred to simply as the processor) and GPU (graphics processing unit, which is the main chip on a video card).

In addition, head-mounted device HMD comprises said computer having virtual reality software to operate virtual reality visual field testing, whereby virtual reality is a completely virtual environment created from a combination of software and compatible hardware. This completely immerses the user, Patient P, into the environment, giving them the ability to interact with the virtual world in a seemingly real way.

Step B) providing a virtual interactive tutorial automatically, comprises an interactive tutorial about what focus/fixation point 30 to look at and clicking when a stimulus light appears. The virtual interactive tutorial is a mini practice before starting the peripheral visual field tests PVFT, wherein Patient P clicks a controller as any stimulus light from stimulus points 50 appear, and when fixation point 30 moves to new locations and new stimulus points 50 appear.

Step C) beginning the peripheral visual fields test PVFT automatically after the virtual interactive tutorial, is the part of the test when the tutorial is over and a real peripheral visual field test PVFT begins.

Step D) showing fixation point 30 at a first location of field of view 22 automatically for patient P to focus on for a duration of the peripheral visual field test PVFT, comprises fixation point 30, which appears at a first location, and patient P focusing on fixation point 30.

Step E) displaying a first sequence of stimuli points 50 for the first location of fixation point 30 automatically, comprises the appearance of a sequence of stimuli points 50. Stimuli points 50 blink/flash or move in predetermined locations or vectors.

Step F) clicking on a trigger of a controller by patient P when stimuli points 50 are seen, comprises an action by patient P of clicking a trigger of a controller every time that stimuli points 50 are seen.

Step G) showing fixation point 30 at a second location of field of view 22 automatically for patient P to focus on for the duration of peripheral visual field test PVFT, comprises a second appearance of fixation point 30 at a different location where patient P should focus. A single fixation point 30 appears at a time.

Step H) displaying a second sequence of stimuli points 50 for the second location of fixation point 30 automatically, comprises the appearance of another sequence of stimuli points 50 for the second location of fixation point 30.

Step I) clicking on the trigger of the controller by patient P when stimuli points 50 are seen, comprises an action by patient P of clicking a trigger of a controller every time that stimuli points 50 are seen.

Step J) showing fixation point 30 at a third location of field of view 22 automatically for patient P to focus on for the duration of peripheral visual field test PVFT, comprises a third appearance of fixation point 30 at another different location where patient P should focus.

Step K) displaying a third sequence of stimuli points 50 for the third location of fixation point 30 automatically, comprises the appearance of another sequence of stimuli points 50 for the third location of fixation point 30.

Step L) clicking on the trigger of the controller by patient P when stimuli points 50 are seen comprises an action by patient P of clicking a trigger of a controller every time that stimuli points 50 are seen.

Step M) placing fixation point 30 at additional different locations sequentially and automatically until all predetermined sequences of stimuli points 50 have been tested, comprises the appearance of fixation point 30 in multiple different locations of field of view 22 to test predetermined sequences of stimuli points 50 in multiple areas.

Step N) ending the peripheral visual field test PVFT comprises that all predetermined sequences of stimuli points 50 have been tested and the test is finished.

Present invention 10 is therefore an automated method using a specific system that comprises head-mounted device HMD.

Figure 2A:
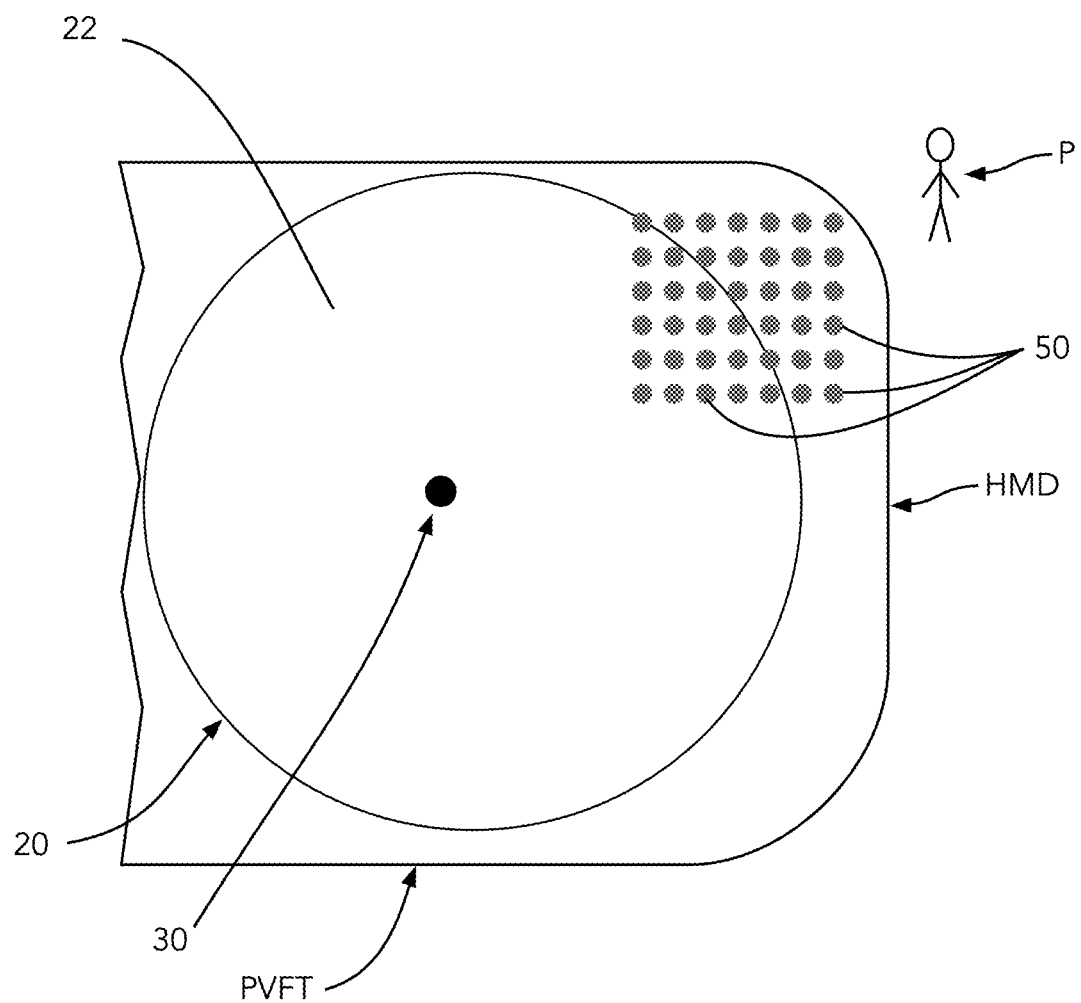
FIG. 2A is a prior art diagram representing a field of view on one side of a head-mounted device having a fixation point at a center and stimuli points outside of a field of view.

Seen in FIG. 2A is a prior art diagram, whereby one side of head-mounted device HMD has a limited field of view (FoV) 22. Usually, when patient P takes a prior art visual field test PVFT, they stare and focus on fixation point 30 at a center of display 20 while individual stimuli points 50 and lights flash around center fixation point 30 at different locations. In the case of peripheral visual fields, if fixation point 30 is still at the center, some stimuli points 50 will be outside of field of view 22, and only the closer stimulus points 50 can be seen.

Figure 2B:
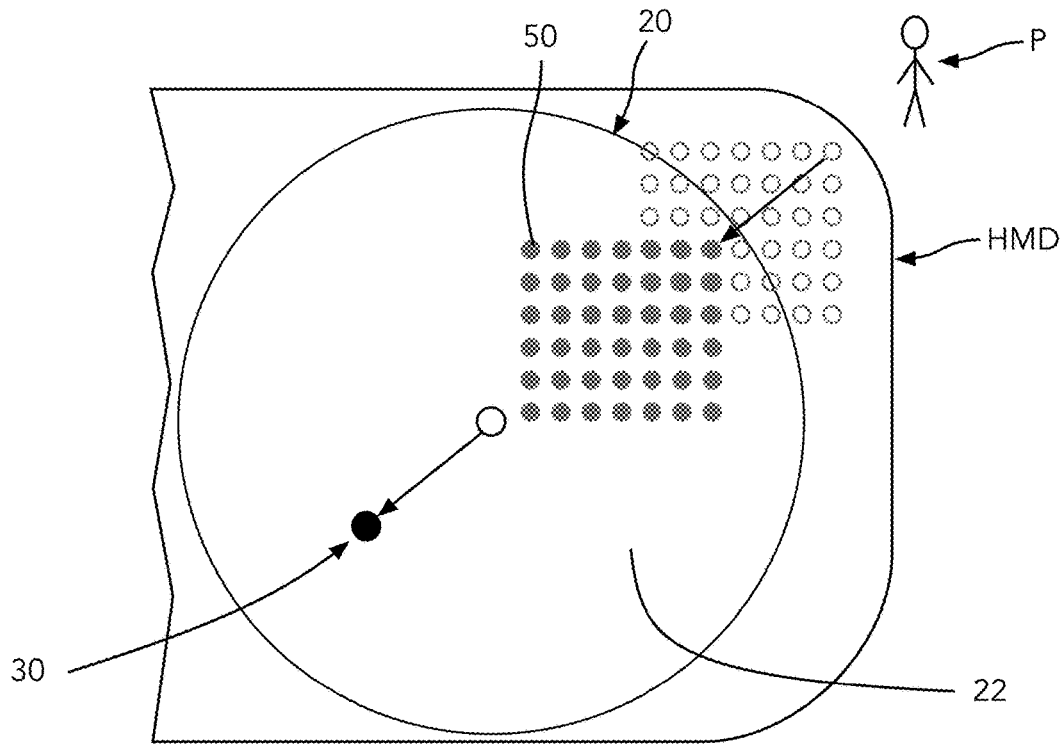
FIG. 2B is a diagram representing a field of view on one side of the head-mounted device having the fixation point moved to another location and all stimuli points within the field of view.

As seen in FIG. 2B, after moving fixation points 50 to a different location, all within display 20, then all stimulus points 50 relative to the new fixation point 30 appear within field of view 22. Present invention 10 comprises a method, wherein fixation point 30 is placed at multiple areas of field of view 22 for testing stimuli points 50 that are outside of field of view 22 when fixation point 30 initially is at the center of display 20. Present invention 10 may be applied as a Visual Field Diagnostic tool for Ptosis disorders, Esterman tests, or any expanded peripheral Visual Field tests.

Figure 3:
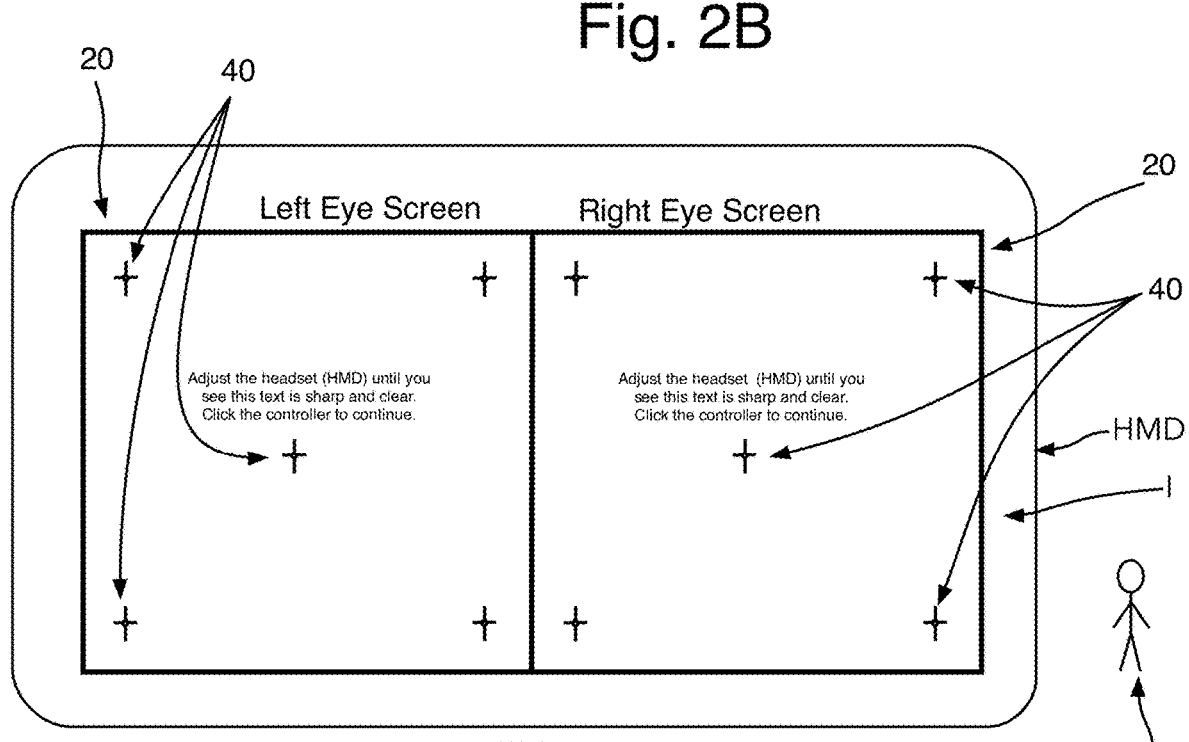
FIG. 3 is a graphic representation of a left eye screen and a right eye screen of the head-mounted device showing virtual features.

As seen in FIG. 3, virtual introduction I is through audio, virtual images/videos, and text. Head-mounted device HMD adjustment involves a visual clarity and comfort of head-mounted device HMD, wherein patient P should have an optimal viewing of virtual reality (VR) tests. Displays for adjusting head-mounted device HMD provide visual features 40 to make sure everything is clear for patient P. In a preferred embodiment, visual features 40 are crosshairs showed at predetermined points of display 20 or a large circle. In a preferred embodiment, the crosshairs are five crosshairs for each eye screen. If visual features 40 are blurry in any way, patient P can adjust head-mounted device HMD to make sure visual features 40 become clear and crisp.

Figure 4:
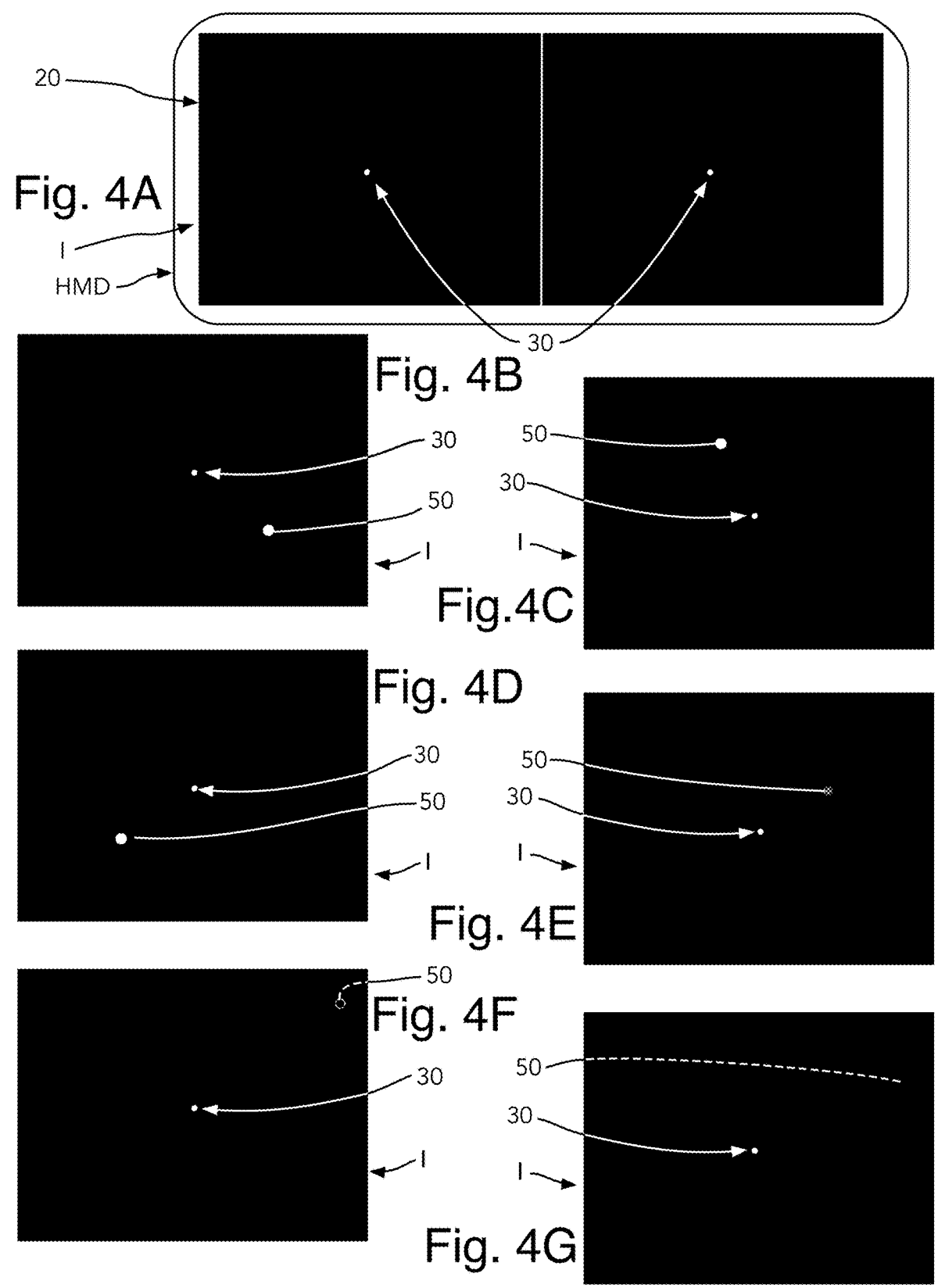
FIG. 4A is a graphic representation of the left eye screen and the right eye screen of the head-mounted device showing fixation points.
FIG. 4B is a graphic representation of an eye screen on one side of a head-mounted device showing a fixation point and a stimuli point that is seen by a patient at a first area close to a fixation point.
FIG. 4C is a graphic representation of an eye screen on one side of the head-mounted device showing a fixation point and a stimuli point that is seen by the patient at a second area close to the fixation point.
FIG. 4D is a graphic representation of an eye screen on one side of the head-mounted device showing a fixation point and a stimuli point that is seen by the patient at a third area close to the fixation point.
FIG. 4E is a graphic representation of an eye screen on one side of the head-mounted device showing a fixation point and a stimuli point that is less visible for the patient.
FIG. 4F is a graphic representation of an eye screen on one side of the head-mounted device showing a fixation point and a stimuli point that is not seen by the patient at a first peripheral area.
FIG. 4G is a graphic representation of an eye screen on one side of the head-mounted device showing a fixation point and a stimuli point that is not seen by the patient at a second peripheral area.

FIG. 4A is graphic representation of a left eye screen and a right eye screen of head-mounted device HMD showing fixation points 30, whereby virtual instructions I include showing fixation points 30 on display 20. More specifically, virtual instructions I include showing fixation points 30 on display 20 for patient P to focus on for an entirety of peripheral visual field test PVFT. Fixation points 30 appear at different locations of screen 20. Patient P is instructed to focus on fixation points 30 for the duration of the exam. Fixation points 30 are displayed as an image or a colored light. In a preferred embodiment, fixation points 30 are displayed as a glowing and dampening colored light. Patient P may perform a monocular or binocular viewing of fixation points 30, whereby Patient P can have one eye viewing one fixation point 30 with the other occluded, or turned off on head-mounted device HMD, or patient P can have both eyes viewing fixation points 30. The properties of glowing, movement, and binocular fixation are incorporated to enhance focus and fixation on fixation points 30 because it is critical for the test. Additionally, each fixation point 30 is showed at multiple locations. This helps to replicate dynamic locations where fixation point 30 may appear during testing.

FIGS. 4B, 4C, 4D, 4E, 4F, and 4G are graphic representations of an eye screen on one side of head-mounted device HMD, as seen in FIG. 4A. Virtual instructions I further comprise showing patient P the appearance and location of stimuli points 50. As an example, stimuli points 50 are presented as a single point of light that blinks on and off. The virtual interactive tutorial comprises a mini sequence combining a fixation point 30 and stimuli points 50, for each eye screen, to replicate a real peripheral visual field test PVFT, whereby stimuli points 50 are presented at a surrounding area around each fixation point 30. Patient P may clearly see stimuli points 50, as best seen in FIGS. 4B, 4C, and 4D, or may not have a clear visualization of stimuli point 50, as best seen in FIG. 4E. In addition, as seen in FIGS. 4F and 4G, stimuli points 50 may not be seen by patient P at all. During the virtual interactive tutorial, each fixation point 30 is placed in a first location and stimuli points 50 in another, patient P clicks when stimuli points 50 are seen. Stimuli points 50 may move or be static. If fixation point 30 is moved to a second location, stimuli points 50 also move, whereby patient P clicks each time that stimuli points 50 are seen. This sequence sets expectations for patient P on reaction time for a "positive" trigger and click.

Figure 5:
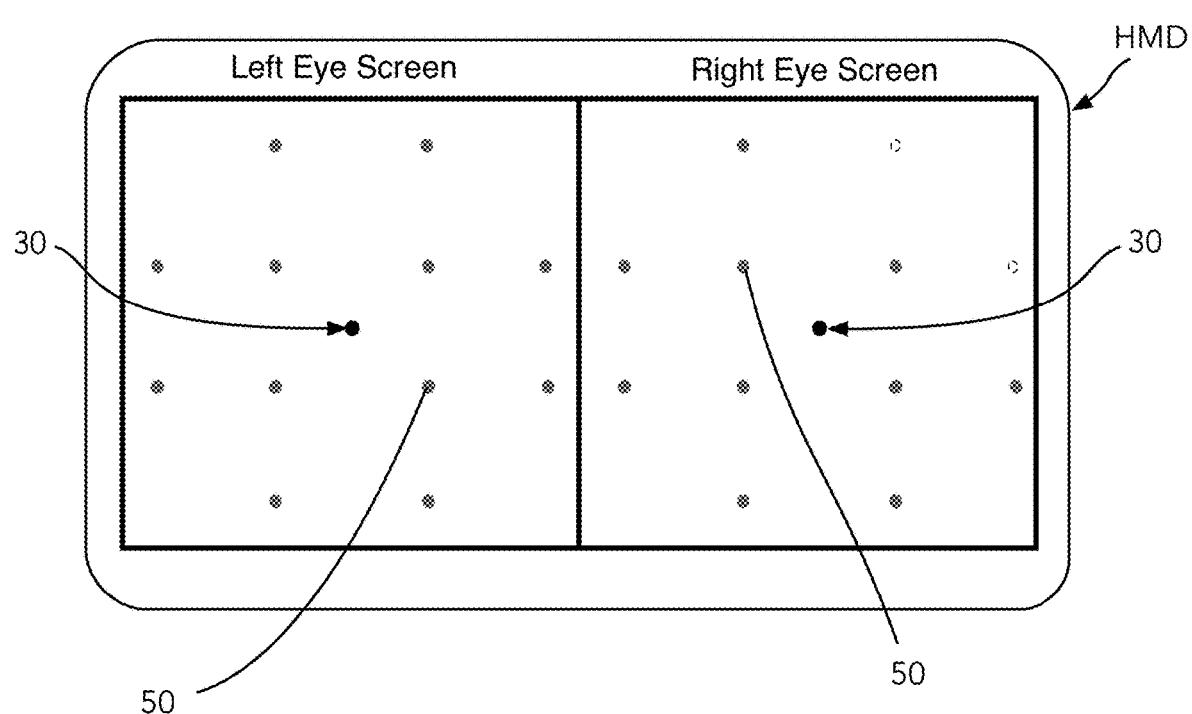
FIG. 5 is a graphic representation of a left eye screen and a right eye screen of the head-mounted device showing fixation points and a plurality of stimulus points.

Seen in FIG. 5 is graphic representation of a left eye screen and a right eye screen of head-mounted device HMD showing fixation points 30 and a plurality of stimulus points 50. Instructions are given to patient P to remain focused on fixation points 30 and to click/press trigger whenever example stimulus points 50 are seen, whereby stimuli points 50 are shown at different light decibels.

Figure 6:
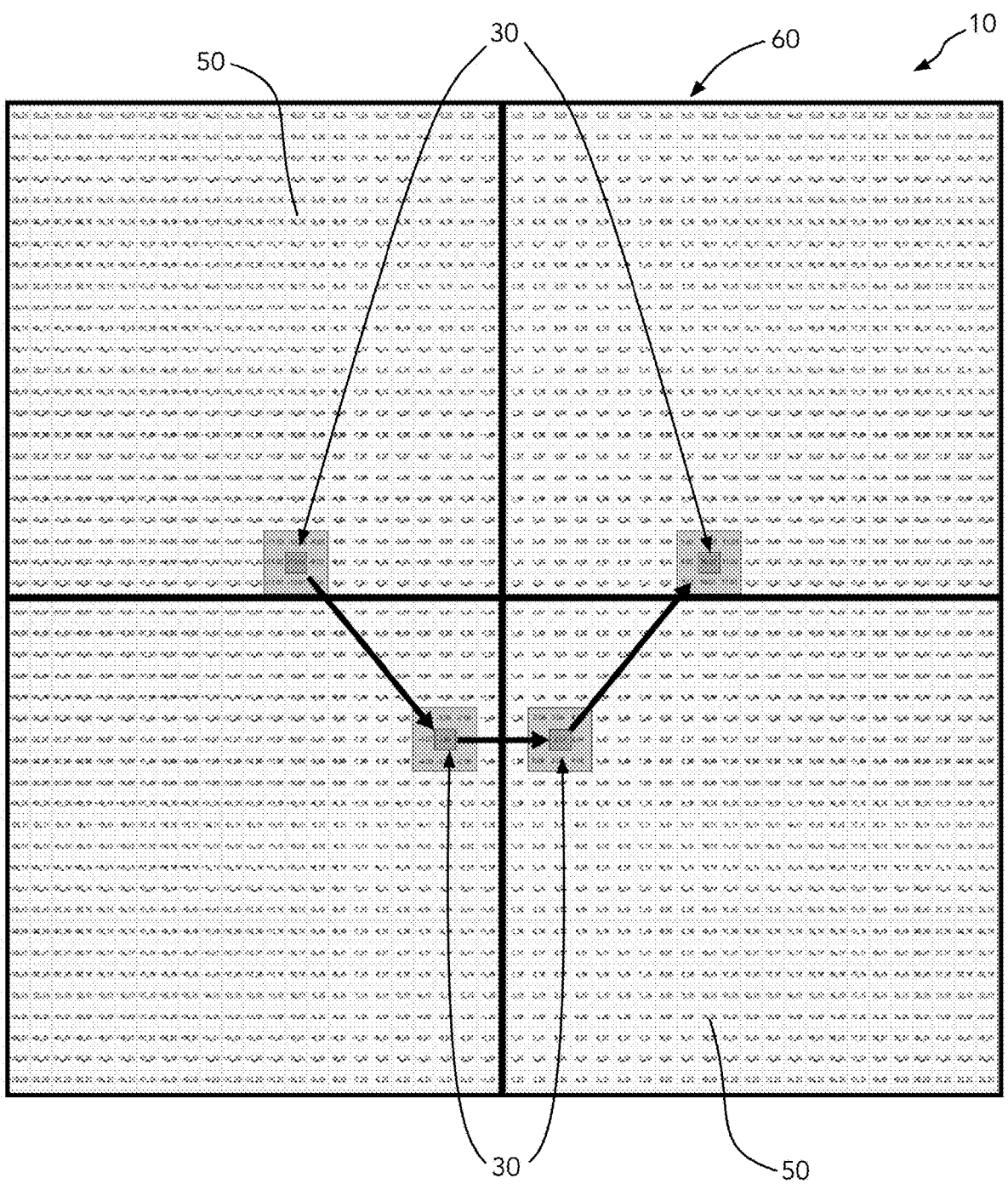
FIG. 6 is a graphic representation of a grid showing fixation points at different locations.
Figure 7:
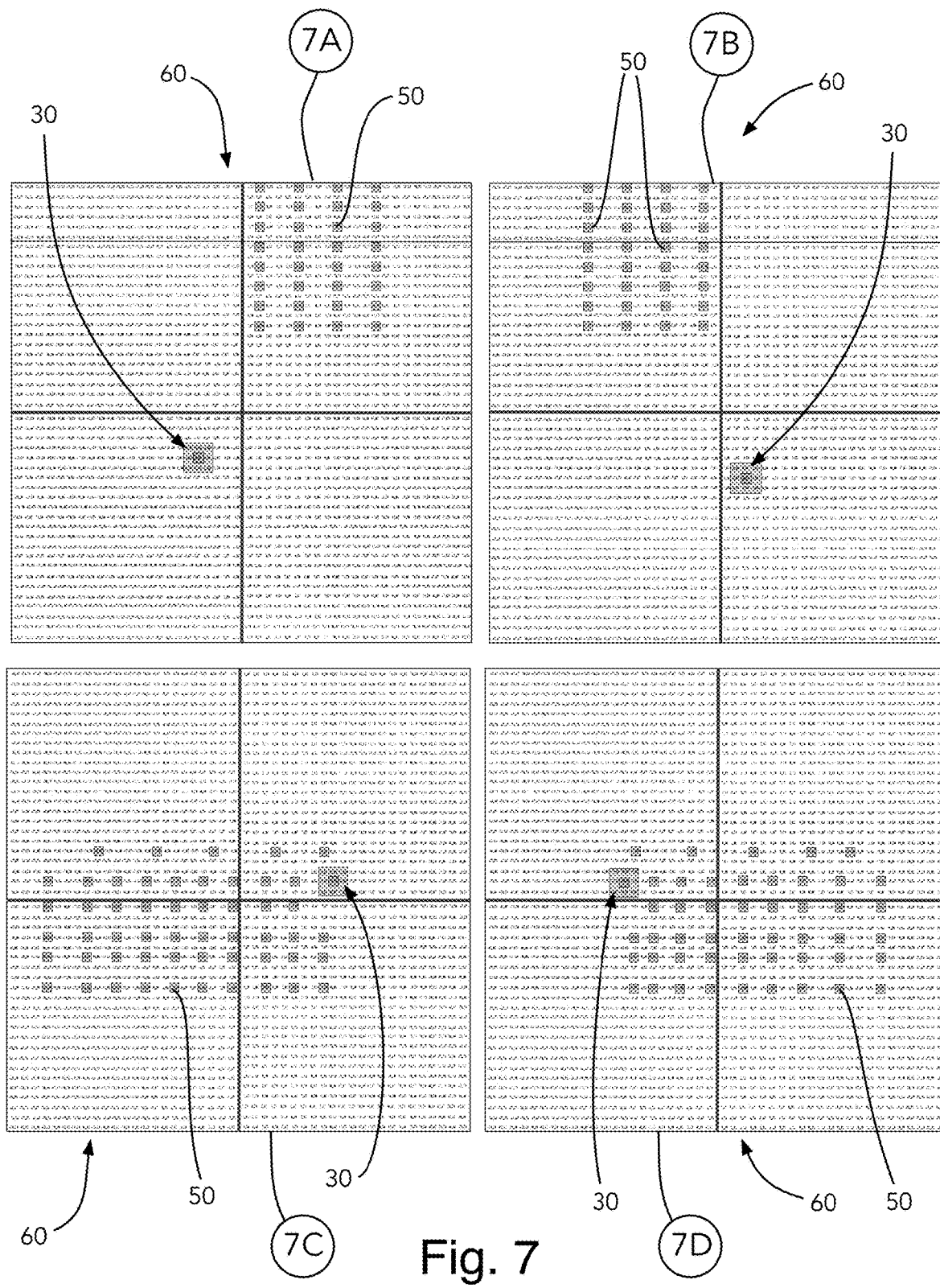
FIG. 7 is a graphic representation of grids showing fixation points at different locations and groupings of stimuli points that appear at opposite sides of corresponding fixation points.
Figure 7A:
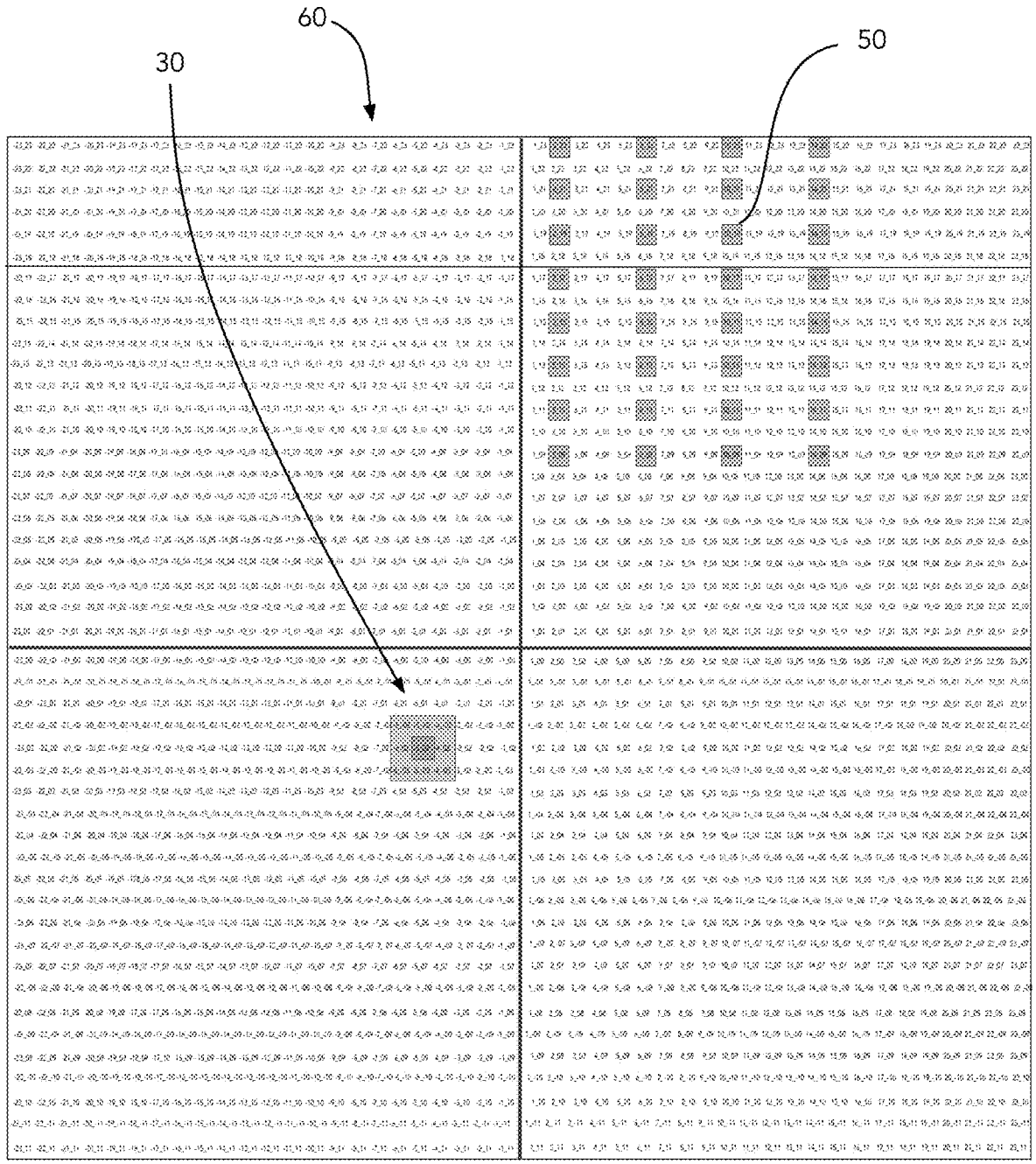
FIG. 7A is a close up graphic representation of grid 7 showing fixation points at different locations and groupings of stimuli points that appear at opposite sides of corresponding fixation points.
Figure 7B:
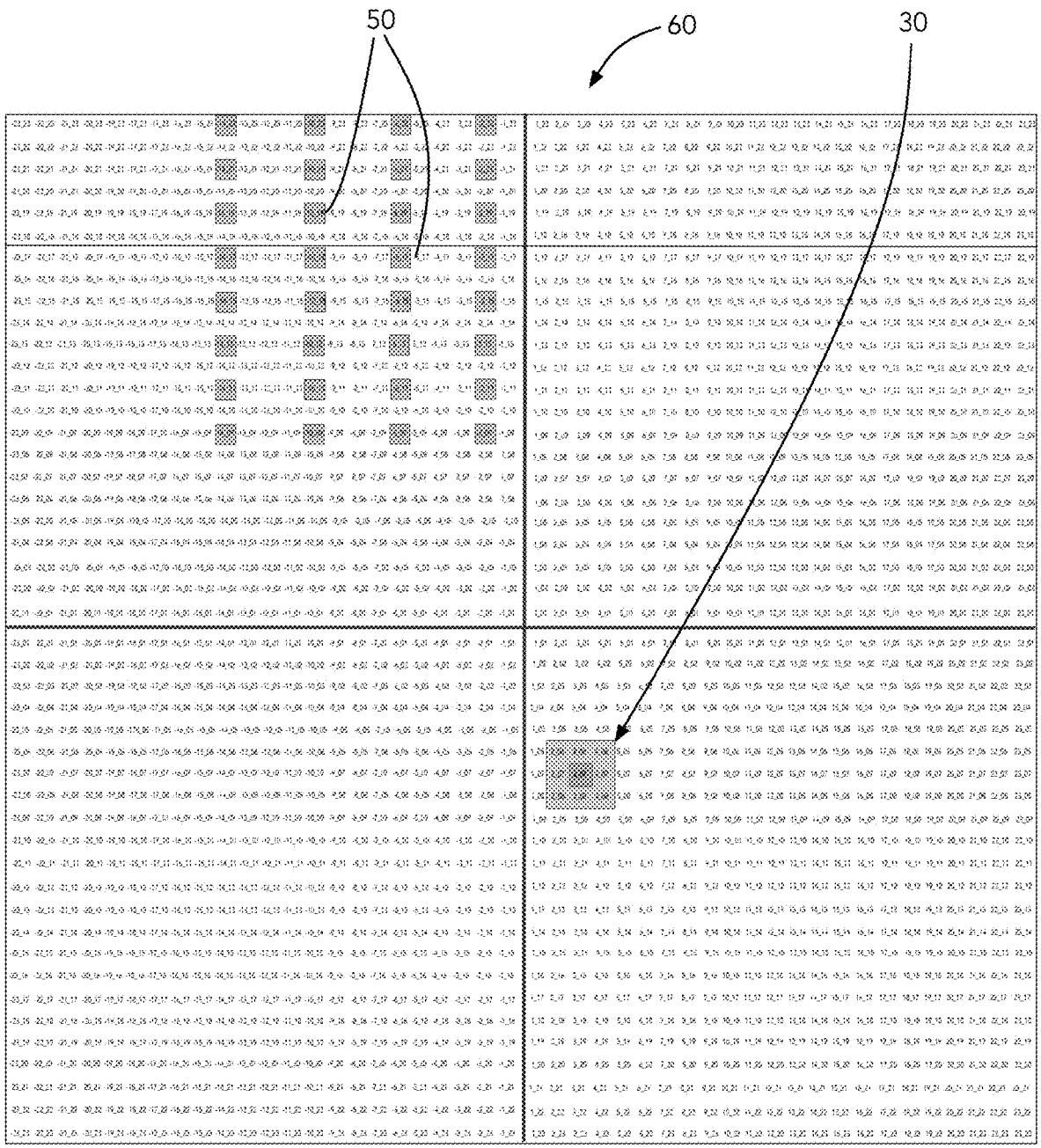
FIG. 7B is a close up graphic representation of grid 7 showing fixation points at different locations and groupings of stimuli points that appear at opposite sides of corresponding fixation points.
Figure 7C:
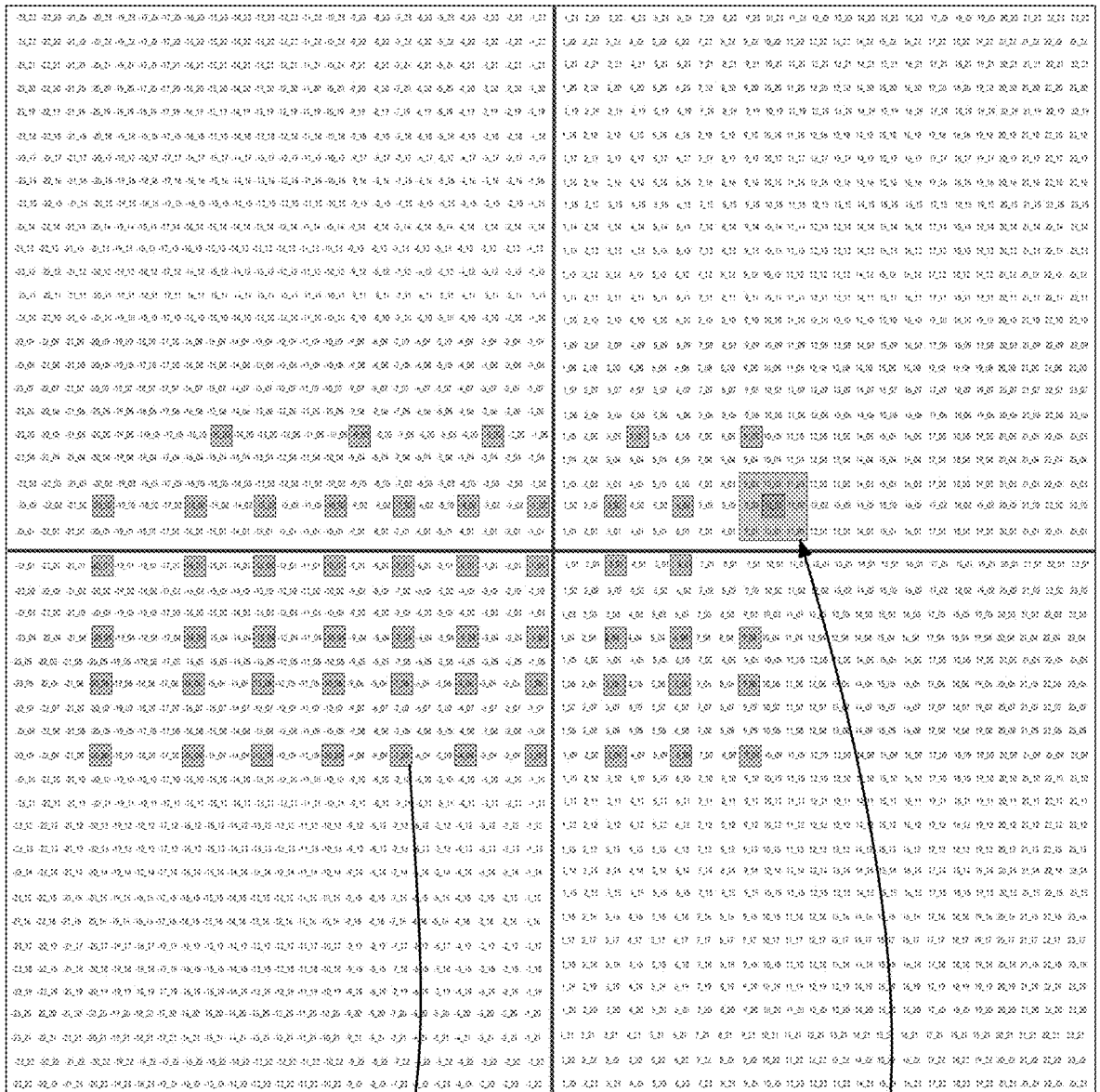
FIG. 7C is a close up graphic representation of grid 7 showing fixation points at different locations and groupings of stimuli points that appear at opposite sides of corresponding fixation points.
Figure 7D:
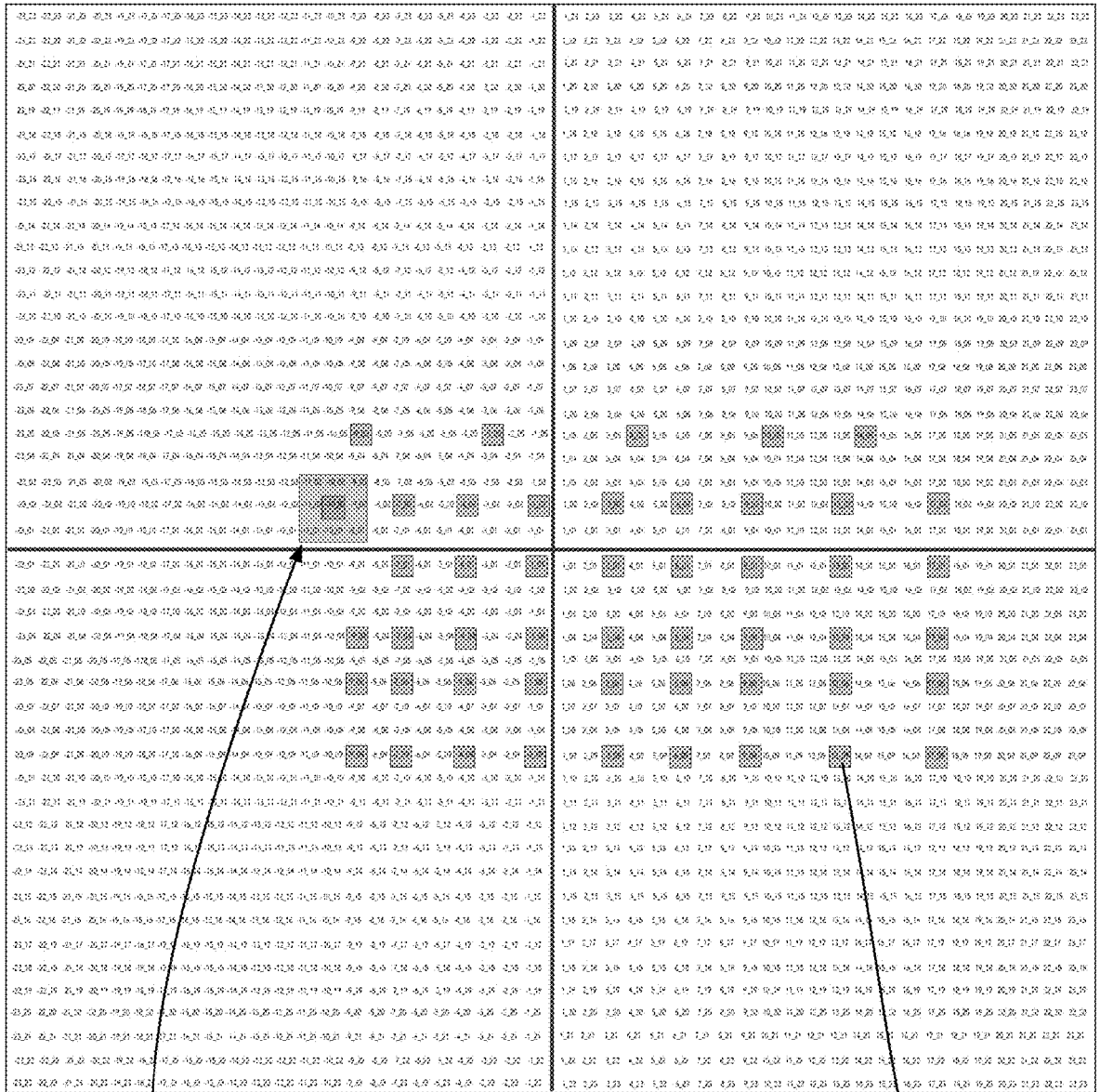
FIG. 7D is a close up graphic representation of grid 7 showing fixation points at different locations and groupings of stimuli points that appear at opposite sides of corresponding fixation points.

As seen in FIGS. 6 and 7, present invention 10 comprises a pre-set sized grid of points 60, whereby stimuli points 50 are part of grid of points 60 and are spaced apart a predetermined distance. Stimuli points 50 produce a light stimulus and follow a semi-random schedule for appearance. In operation, a single fixation point 30 is displayed at a time. Fixation point 30 is removed or moved to another location after testing a corresponding sequence of stimuli points 50. When fixation point 30 is removed, another fixation point 30 is displayed afterwards at a different location with a new corresponding grouping of stimuli points 50. Therefore, fixation point 30 is moved to different locations of grid of points 60 allowing to open different parts of the visual field. As an example, when fixation point 30 is moved lower in grid of points 60, this allows for more stimuli points 50 to be tested in the Upper Visual Field of patient P.

As best seen in FIG. 7, each stimuli point 50 forms one single part of a group of stimuli points 50 at a particular location. These groups of stimuli points 50 are associated with a location of fixation point 30. Stimuli points 50 appear on an opposite side of fixation point 30. As an example, if fixation point 30 is on a left side, stimuli points 50 appear on a right side. If fixation point 30 is on a bottom, stimuli points 50 appear on a top.

FIGS. 7A, 7B, 7C, and 7D are close up graphic representations of grid 7 showing fixation points at different locations and groupings of stimuli points that appear at opposite sides of corresponding fixation points.

Figure 8:
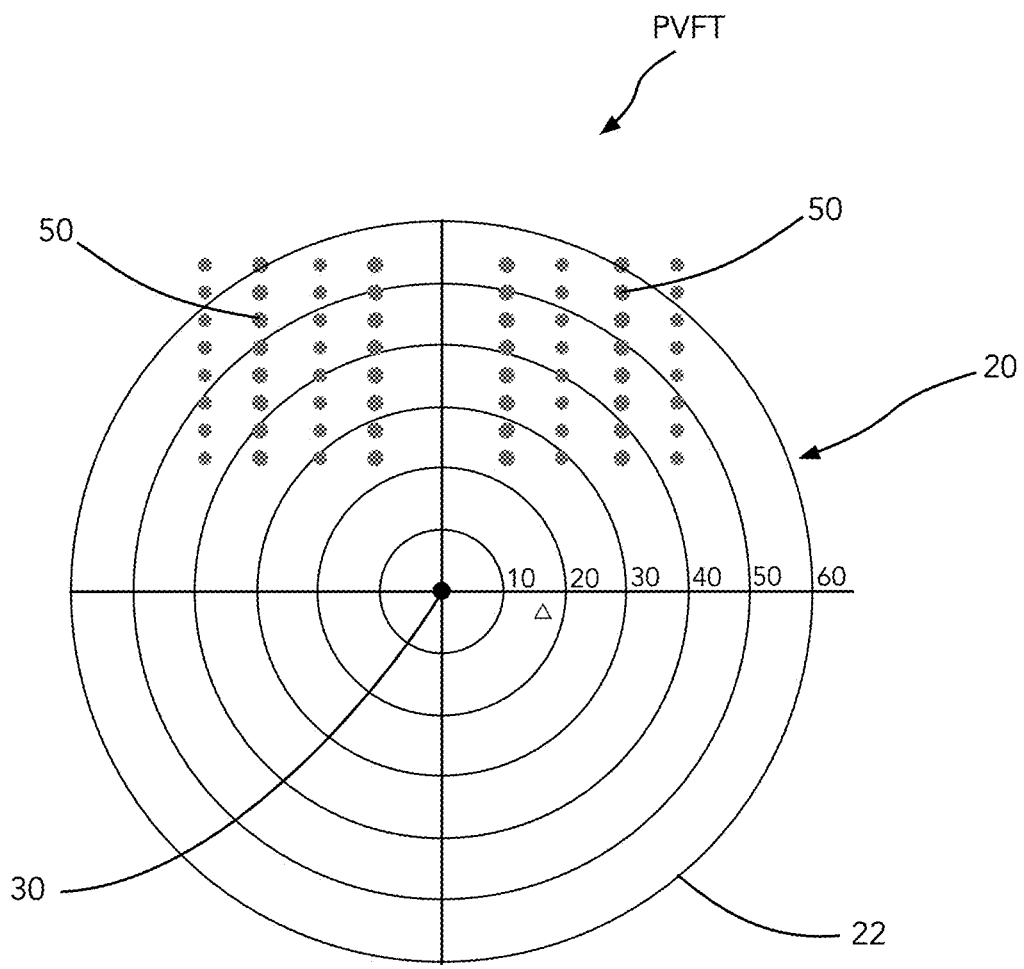
FIG. 8 is a Screening Test Pattern of a right eye using Static Screening Strategy.
Figure 9A:
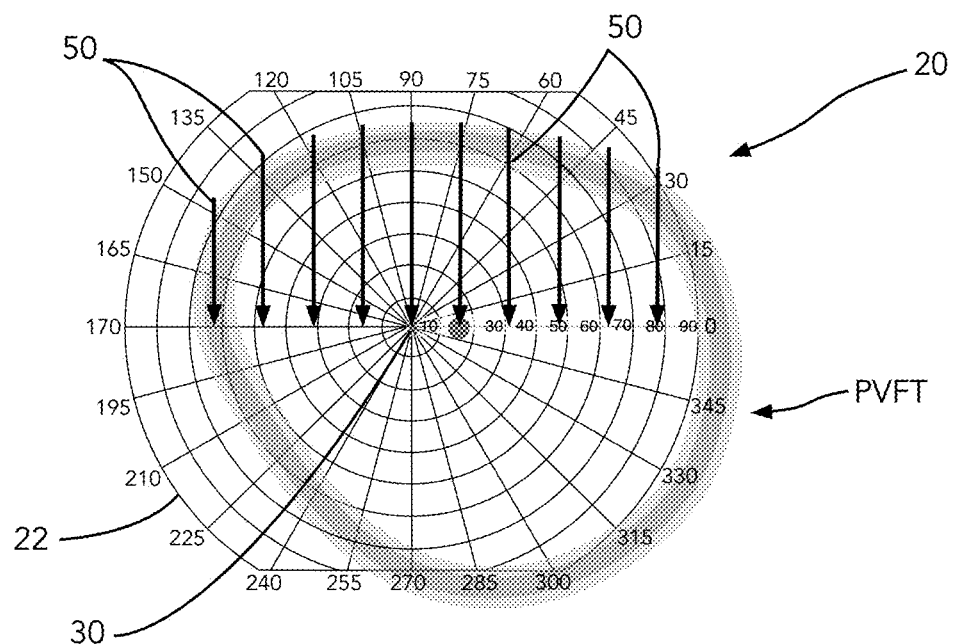
FIG. 9A is a graphic representation of a Ptosis template for an automated kinetic perimetry test.
Figure 9B:
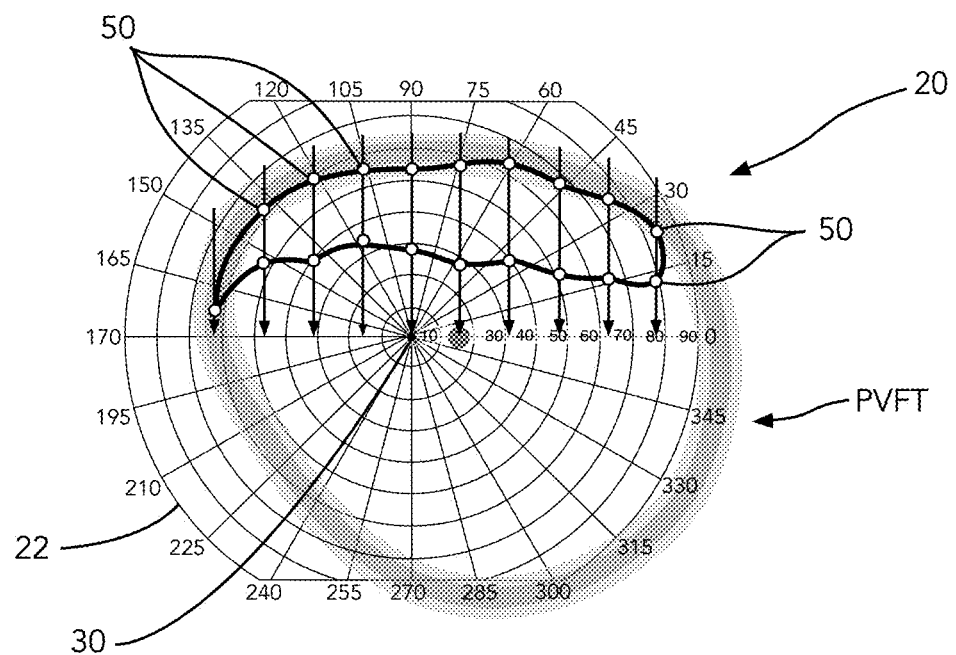
FIG. 9B is a graphic representation of an automated kinetic perimetry test for Ptosis.

As seen in FIGS. 8, 9A and 9B, light stimulus from stimuli points 50 may be static or dynamic, whereby light stimulus from stimuli points 50 may be static and shown in one location, or they can be dynamic and move to predetermined locations.

During Peripheral Visual Field Test PVFT, stimuli of light are shown at different locations of field of view 22 to diagnose whether patient P can see a light at a particular part of their Visual Field. As seen in FIG. 8, an example of a method following Static Screening Strategy comprises the steps of:

i. staring at fixation point 30 by patient P for a duration of an exam;
 ii. showing static stimuli points 50 at a fixed location;
 iii. showing a light stimulus at a certain light decibel level for a short duration.

Stimuli points 50 are tested several times. If stimuli points 50 are seen, a positive response is recorded. If stimuli points 50 are not seen, a negative response is recorded. If a response to stimuli points 50 differ, then it is tested once more, and the last response is the tiebreaker.

As seen in FIGS. 9A and 9B, an example of a method following Dynamic Screening Strategy comprises the steps of:

i. staring at fixation point 30 by patient P for a duration of an exam;

ii. moving stimuli points 50 to different locations on display 20;

iii. moving stimuli points 50 to a different area when patient P cannot see stimuli points 50.

If stimuli points 50 are at an area not seen because they appear outside of a field of view 22, are at a blind spot, or because of scotoma, stimuli points 50 are then moved into an area where they can be seen by patient P. Each point and location at which stimuli points 50 go from unseen to seen is logged and charted. The process is then repeated to verify the location that stimuli points 50 were first seen.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An automated method for testing peripheral and expanded visual fields on limited field of view head-mounted device, comprising the steps of:
    A) displaying a virtual introduction on performing a peripheral visual field test on a head-mounted device, whereby said head-mounted device comprises a computer having virtual reality software to operate virtual reality visual field testing;
    B) providing a virtual interactive tutorial automatically;
    C) beginning said peripheral visual fields test automatically after said virtual interactive tutorial;
    D) showing a fixation point at a first location of a field of view automatically for a patient to focus on for a duration of said peripheral visual field test;
    E) displaying a first sequence of stimuli points for said first location of said fixation point automatically;
    F) clicking on a trigger of a controller by said patient when said stimuli points are seen;
    G) showing said fixation point at a second location of said field of view automatically for said patient to focus on for the duration of said peripheral visual field test;
    H) displaying a second sequence of said stimuli points for said second location of said fixation point automatically;
    I) clicking on said trigger of said controller by said patient when said stimuli points are seen;
    J) showing said fixation point at a third location of said field of view automatically for said patient to focus on for the duration of said peripheral visual field test;
    K) displaying a third sequence of stimuli points for said third location of said fixation point automatically;
    L) clicking on said trigger of said controller by said patient when said stimuli points are seen;
    M) placing said fixation point at additional different locations sequentially and automatically until all predetermined sequences of said stimuli points have been tested;
    N) ending said peripheral visual field test.

2. The automated method for testing peripheral and expanded visual fields on limited field of view head-mounted device set forth in claim 1, wherein said virtual introduction comprises instructions about said fixation point, said stimuli points, a head-mounted device adjustment, and a controller adjustment.

3. The automated method for testing peripheral and expanded visual fields on limited field of view head-mounted device set forth in claim 1, wherein said virtual introduction is through virtual graphics, virtual images, audio, and text.

4. The automated method for testing peripheral and expanded visual fields on limited field of view head-mounted device set forth in claim 1, wherein said fixation point is displayed as an image or a colored light.

5. The automated method for testing peripheral and expanded visual fields on limited field of view head-mounted device set forth in claim 1, wherein said fixation point is displayed as a glowing and dampening colored light.

6. The automated method for testing peripheral and expanded visual fields on limited field of view head-mounted device set forth in claim 1, wherein said fixation point is animated.

7. The automated method for testing peripheral and expanded visual fields on limited field of view head-mounted device set forth in claim 1, wherein said patient views a monocular or binocular viewing of said fixation point.

8. The automated method for testing peripheral and expanded visual fields on limited field of view head-mounted device set forth in claim 1, wherein a single said fixation point is displayed at a time.

9. The automated method for testing peripheral and expanded visual fields on limited field of view head-mounted device set forth in claim 1, wherein said fixation point is automatically removed or moved after testing a corresponding sequence of said stimuli points.

10. The automated method for testing peripheral and expanded visual fields on limited field of view head-mounted device set forth in claim 1, wherein said stimuli points produce a light stimulus.

11. The automated method for testing peripheral and expanded visual fields on limited field of view head-mounted device set forth in claim 1, wherein said stimuli points are dynamic or static.

12. The automated method for testing peripheral and expanded visual fields on limited field of view head-mounted device set forth in claim 1, wherein said stimuli points automatically blink or move to predetermined locations.

13. The automated method for testing peripheral and expanded visual fields on limited field of view head-mounted device set forth in claim 1, wherein said stimuli points are part of a grid of points.

14. The automated method for testing peripheral and expanded visual fields on limited field of view head-mounted device set forth in claim 13, wherein said grid of points has a predetermined size.

15. The automated method for testing peripheral and expanded visual fields on limited field of view head-mounted device set forth in claim 13, wherein said stimuli points on said grid of points are automatically spaced a predetermined distance.

16. The automated method for testing peripheral and expanded visual fields on limited field of view head-mounted device set forth in claim 1, wherein said stimuli points are automatically grouped.

17. The automated method for testing peripheral and expanded visual fields on limited field of view head-mounted device set forth in claim 1, wherein said fixation point is associated with a grouping of said stimuli points.

18. The automated method for testing peripheral and expanded visual fields on limited field of view head-mounted device set forth in claim 1, wherein said stimuli points follow a semi-random schedule for appearance.

19. The automated method for testing peripheral and expanded visual fields on limited field of view head-mounted device set forth in claim 1, wherein said stimuli points appear on an opposite side of said fixation point on said field of view.

20. The automated method for testing peripheral and expanded visual fields on limited field of view head-mounted device set forth in claim 1, wherein said fixation point is placed in multiple locations of said field of view for testing said stimuli points that are outside of said field of view of a head-mounted device if said fixation point is in the center of said field of view.

* * * * *